United States Patent [19]

Liebrenz et al.

[11] 4,080,825
[45] Mar. 28, 1978

[54] GLUE BOND TESTER

[75] Inventors: Allan L. Liebrenz, St. Paul, Minn.;
Verne D. O'Keefe, Roberts, Wis.;
Richard V. Soderberg, St. Paul, Minn.

[73] Assignee: Champion International Corporation, Stamford, Conn.

[21] Appl. No.: 743,609

[22] Filed: Nov. 22, 1976

[51] Int. Cl.² ............................................ G01N 19/04
[52] U.S. Cl. ................................ 73/150 A; 73/88 B
[58] Field of Search ............... 73/88 B, 150 A, 150 R, 73/89

[56] References Cited

U.S. PATENT DOCUMENTS

| 3,082,621 | 3/1963 | Soderholm | 73/88 R X |
| 3,394,588 | 7/1968 | Mohle et al. | 73/150 A |
| 3,412,606 | 11/1968 | Cooper et al. | 73/150 A |
| 3,850,033 | 11/1974 | Schmitt | 73/88 B X |

Primary Examiner—Daniel M. Yasich
Attorney, Agent, or Firm—Evelyn M. Sommer

[57] ABSTRACT

Apparatus to test the strength of a glue bond joint connecting two sheets of paperboard or similar sheet-like material. The apparatus automatically produces the bond, duplicating the production process, and then forces the sheets apart by moving the sheets around a bar and measuring deflection of the assembly to which the bar is attached.

4 Claims, 5 Drawing Figures

GLUE BOND TESTER

BACKGROUND OF THE INVENTION

1. Field of the Invention

This disclosure relates generally to apparatus for quality testing of glued joints for strength, and particularly where the joint is between adjacent pieces of paperboard or similar material.

2. Description of the Prior Art

In the packaging industry, it is commonplace for carton blanks to be shipped as flat blanks from the carton manufacturer's plant. The customer who uses the packaging normally erects and fills the carton and closes it in his own facility. This means there is folding and gluing equipment in the customer's plant and there is a need for quality control to evaluate the glued joines which are created on this closing equipment. At the present time destructive testing is carried out on the sample consisting of two specified pieces of paperboard after preparing the sample by separate equipment or by hand and then transferring it to apparatus which applies pressure to pull the joint apart with measurement of the force required to accomplish that destructive test. There is a need for testing equipment which can prepare the sample so that it accurately reflects the strength obtained by the production equipment and then conduct the test on the same piece of equipment.

SUMMARY OF THE INVENTION

Apparatus having means to uniformly apply adhesive to and join test strips of paperboard including means to apply heat and pressure to set the bond of the adhesive. Also included is automatic means to separate the bonded strips and measure the force required to break the bond, with means provided for recording the values obtained from those measurements.

DETAILED DESCRIPTION OF THE PREFERRED EMBODIMENT

Figure 1:
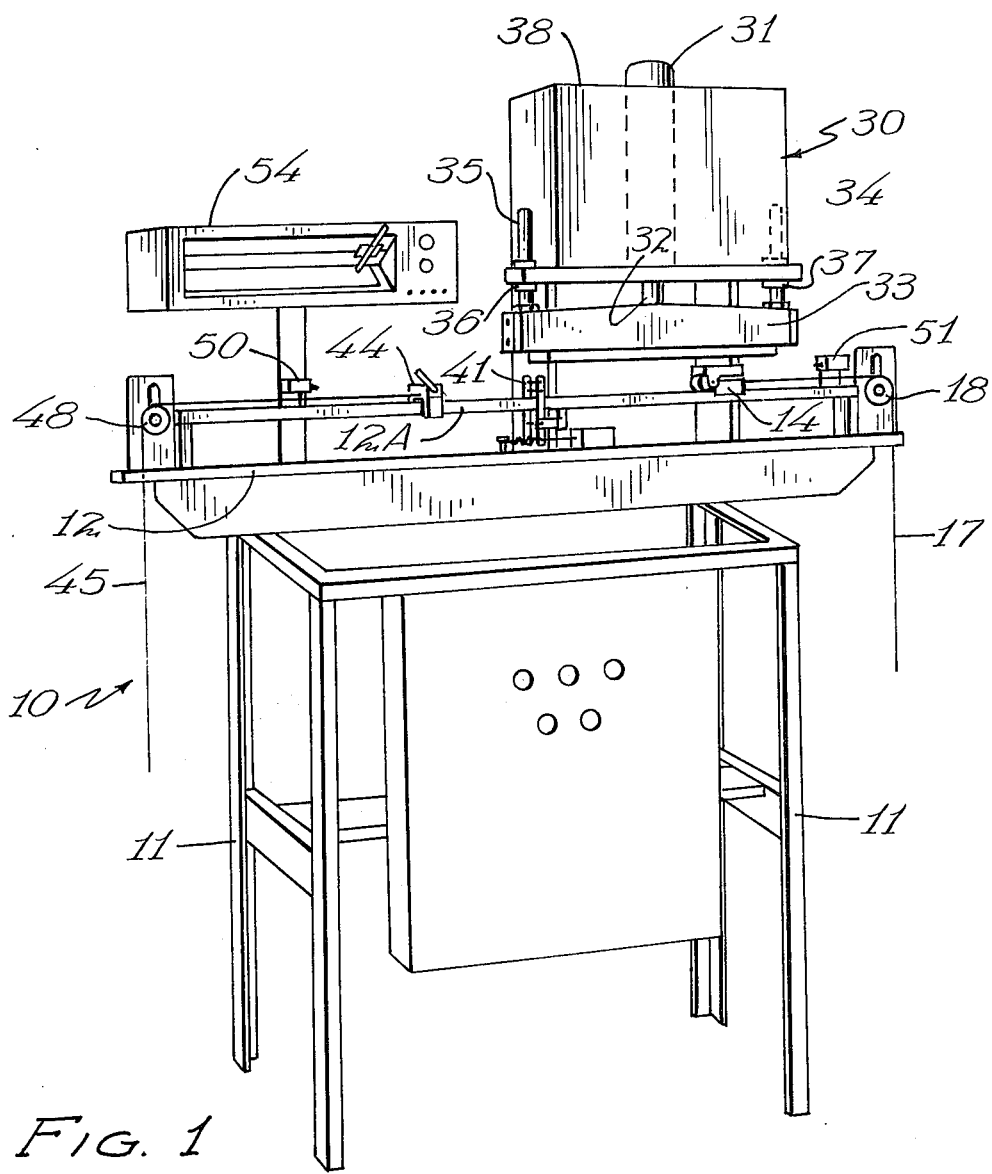
FIG. 1 is a perspective view of the apparatus embodying the present invention.

The overall mechanism 10 is one which for convenience is mounted upon a frame 11 and which includes a base plate 12 to which is attached most of the apparatus. As seen best in FIG. 2, the material to be tested consists of two long narrow strips of paperboard 13 or whatever other material is to be glued. There is provided a means 14 for applying the adhesive in a manner which represents and duplicates the adhesive applicaton which occurs on the closure of a carton in the facility at which the carton is filled and sealed.

Figure 2:
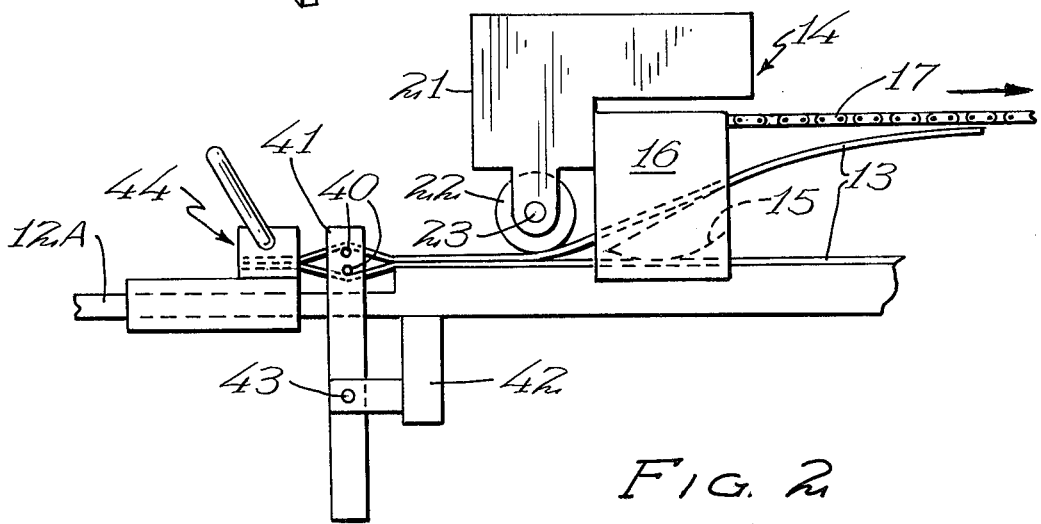
FIG. 2 is a schematic side elevation view of a portion of the apparatus in FIG. 1 showing the salient parts and illustrating how those parts are utilized to apply adhesive to the two test strips and join them together.

This means for applying adhesive 14 includes a metering block 15 which is mounted within a housing or casing 16 and is designed to apply adhesive to the lowermost piece of paperboard 13 in a uniform manner approximating the application which occurs on the carton closing equipment. The housing 16 is advanced to the right of the apparatus as it is shown in the drawings by a chain 17 which is drawn about a pulley 18 seen best in FIG. 3 which may take the form of a geared wheel to engage the chain 17, which wheel 18 is mounted on a shaft 19 to a motor 20 seen in FIG. 5 for advancing the means 14 at the desired predetermined rate. In FIG. 2 it can be seen that there is in addition to the housing 16 a weighted roller assembly 21 which has a cylinder type roll 22 mounted for rotation upon a shaft 23 which presses the two pieces of paperboard 13 into contact with one another to insure close contiguous relationship of the test pieces.

Figure 3:
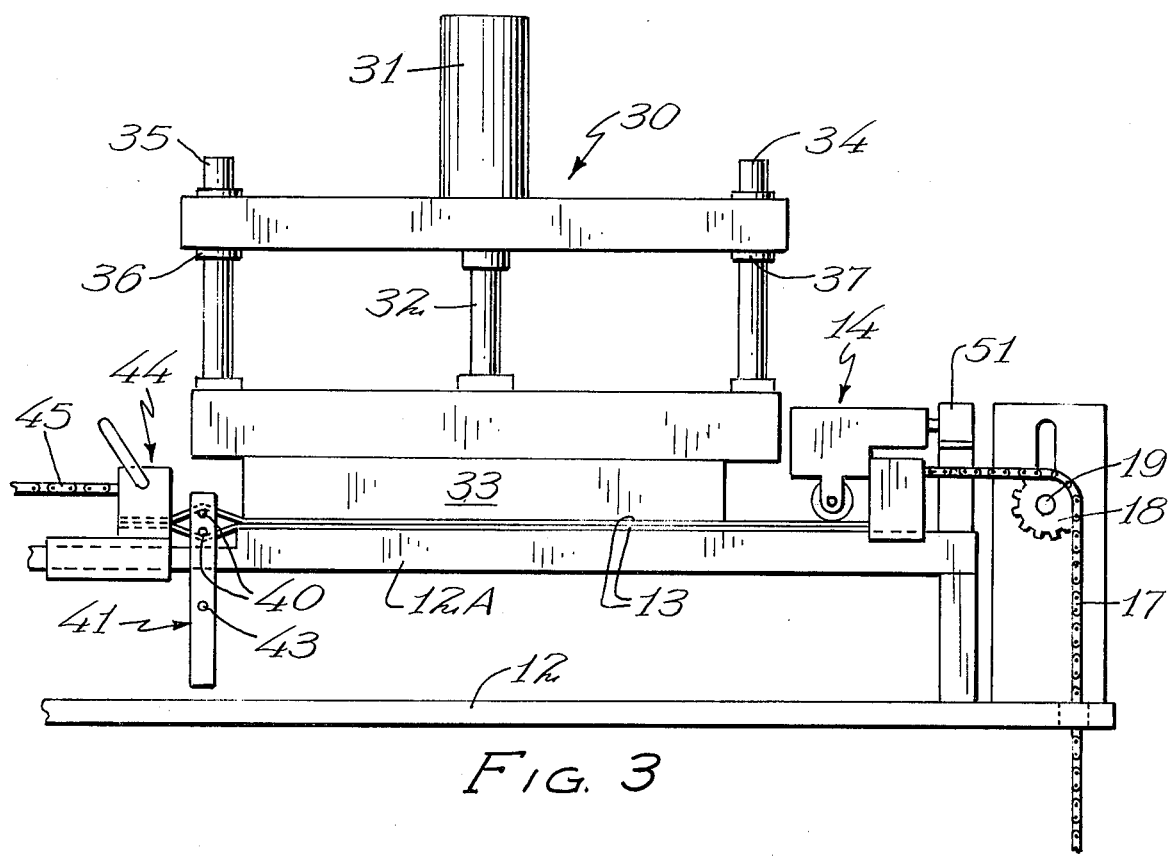
FIG. 3 is a schematic side elevation view of the apparatus in FIG. 1 illustrating how a portion of the apparatus applies heat and pressure to the test seal area.

There is provided in the preferred embodiment means for applying heat and pressure to the glued samples and is shown generally as 30. The means 30 is positioned above the plate 12 which supports the mechanism and includes a hydraulic cylinder or other fluid operated piston 31 which is in turn connected to and operates a piston and rod 32 which is connected to a pressing plate 33. The plate 33 is heated and is kept in vertical alignment by means of guide rods 34 and 35 movable in the bearing sleeves 36 and 37 which are formed as a part of the framing structure 38 seen best in FIG. 1. The pressing plate 33 is electically heated to a predetermined temperature to duplicate the temperatures found on the closing apparatus. The pressure is applied to the sample after it has been glued and after the means 14 for applying adhesive has been moved out of the way to the right as seen in FIG. 3 and is designed to reflect the pressures encountered on the closing equipment. It can be seen in FIG. 3 that the pressing means 30 is designed to be effective over a substantial length of the sample after it has been glued.

As seen best in FIG. 2, an unglued portion of the two sample pieces 13 are positioned about a pair of rotatable rods 40 which are mounted in a separator block 41 that is in turn attached to the frame 12 of the device but is mounted in such a way that it may rotate. This is accomplished by a right angle bracket 42 and a rotatable pin assembly 43 mounted therein. The left or leading end of each of the sample pieces 13 are held together in a clamp block assembly 44 and this clamp block assembly is in turn mounted for slidable movement upon the support beam 12A and is connected by a chain 45 to a drive motor 46 which is positioned on the left side of the apparatus and is seen best in FIG. 3. The drive motor 46 has a geared wheel 47 attached to its shaft 48 and the motor is designed to draw or pull the completed glued sample across the separator block 41 such that the rotating pins 40 separate the previously glued pieces 13.

The travel of the clamp block 44 is restricted and stopped by a limit switch 50 seen best in FIG. 1 which stops power to the motor 46 and prevents over-travel of the apparatus. A similar limit switch is found on the right hand side of the apparatus and is identified as 51, that switch sensing the travel of the metering block 15 and stopping the motor 20 which drives the applicator means 14 and in turn signaling the means for applying pressure 30 that the applicator means 14 is out of the way and the pressure may be applied, by lowering the assembly 30.

The object of this entire mechanism is of course to obtain measurements to help establish quantitative evaluations of the strength of the bond which is being created. This is a function of the operating parameters in the gluing apparatus but also bears some relationship to the adhesive and its particular characteristics as well as the paperboard which is used.

Figure 4:
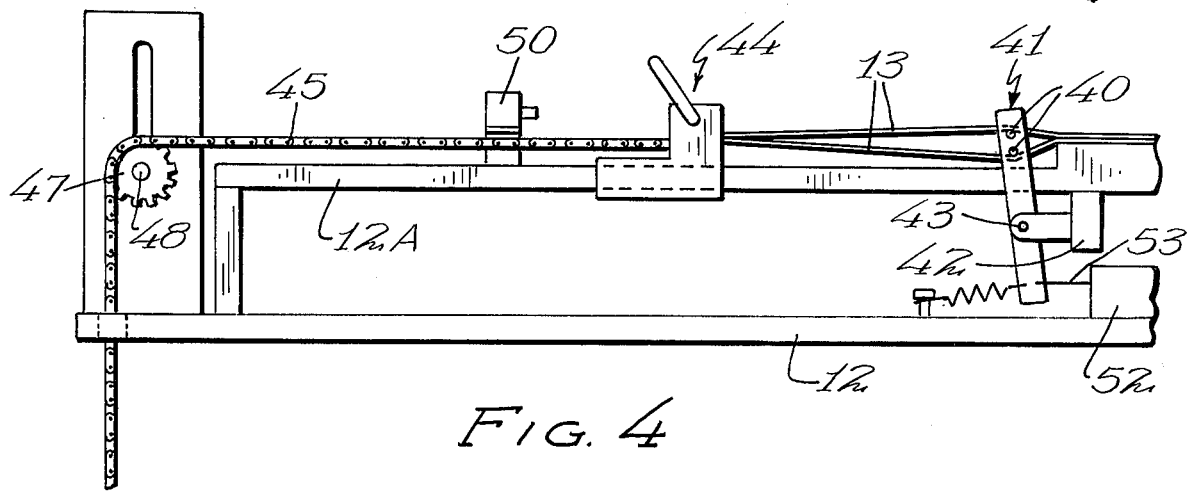
FIG. 4 illustrates in side schematic view how the adhered test strips are drawn past a separator assembly which can pivot and deflect a transducer in order to obtain quantitative measurements relating to the strength of the seal.

These quantitative measurements are obtained by measuring the deflection of the hinged separator block 41 as seen best in FIG. 4 by means of a linear output transducer of the type which gives a different electrical output based on the deflection of the piston which is made a part thereof. The transducer is shown schematically as 52 and the operating piston therein 53. The greater the resistance of the glue bond as the sample is drawn across the separator rods 40, then the greater the deflection of the separator block 41. The particular embodiment shown in FIG. 4 utilizes a spring to keep the separator block 41 in a normal position but it should be understood that there are normally based transducers available wherein the piston 53 is spring loaded. The electrical output from the transducer 52 is directed to and translated into a readout upon a chart recorder device shown generally as 54 in FIG. 1. With consistant and uniform application of adhesive as well as pressure and temperature exerted by the assembly 30, a uniform speed of the clamp block will give chart recordings which may be compared to a norm and provide the user with information of a relative nature as to the quality and character of the adhesive bond which is being produced.

We claim:

1. Apparatus for testing the strength of glued joints between elongated strips of sheet material such as paperboard, said strips of paperboard positioned horizontally and parallel in face-to-face relationship in said apparatus, said apparatus comprising:
    a horizontal base supporting said strips;
    movable clamp block means positioned on said base for gripping a first end of each of said strips and holding them together;
    means for uniformly applying a predetermined amount of adhesive to an upwardly facing surface of the lower to two said strips, said means setting a bond between the material strips at a predetermined temperature by applying the adhesive and being moved away from said movable clamp block means to a position at the opposite end of said strips;
    means for applying heat at a predetermined temperature and pressure to said strips, said means for applying pressure including a pressure plate moved into position against that portion of said strips to which said adhesive has been applied;
    a separator block pivotally mounted on said base;
    a pair of spaced, parallel rotatable separating rods disposed on said separator block and positioned between said strips with a different one of said strips contacting each of said rotatable rods, one of said rods being disposed above the glue line of the adhered strips, and the other rod being disposed below the glue line of the adhered strips;
    means for advancing said clamp block means and said strips at a predetermined rate of movement such that said strips are forced apart, after they have been adhered, as they pass over and under said separating rods;
    means biasing said pivotally mounted separator block into a predetermined normal position; and
    means for quantitatively measuring the deflection of said separator block from said normal position as the force exerted by the separating rods on the glued strips for separating said strips causes the separator block to pivot.

2. The apparatus of claim 1 wherein said clamp block means is advanced along said base by a constant speed motor.

3. The apparatus of claim 1 wherein said means for applying adhesive includes a metering block beneath which said adhesive is distributed onto said lower strip.

4. The apparatus of claim 3 further including a motor to move said means for applying adhesive at a constant rate across the surface of said lower strip.

* * * * *

UNITED STATES PATENT AND TRADEMARK OFFICE
CERTIFICATE OF CORRECTION

PATENT NO. : 4,080,825

DATED : March 28, 1978

INVENTOR(S) : A.L. Liebrenz; V.D. O'Keefe; R. V. Soderberg

It is certified that error appears in the above—identified patent and that said Letters Patent are hereby corrected as shown below:

Column 1, line 16, delete "joines" and insert in lieu thereof -- joints -- .

Figure 5:
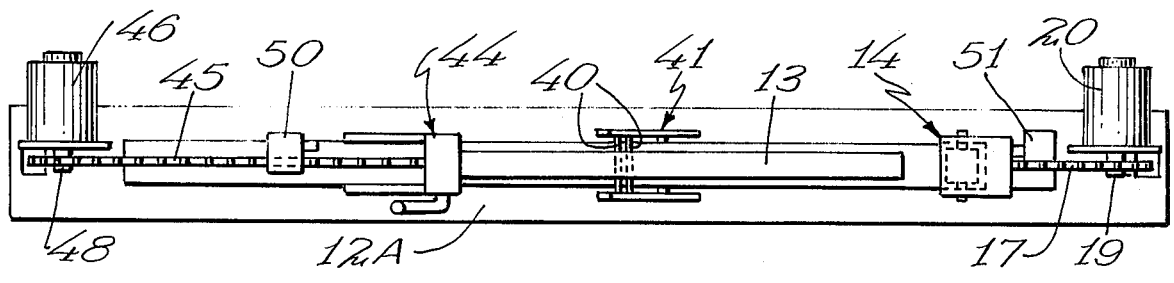
FIG. 5 is a plan view of a portion of the apparatus shown in FIG. 1 illustrating the drive motors and assembly employed in the present invention.

Column 2, line 53, delete "Fig. 3" and insert in lieu thereof -- Fig. 5 -- .

Signed and Sealed this

Fourteenth Day of November 1978

[SEAL]

*Attest:*

RUTH C. MASON
*Attesting Officer*

DONALD W. BANNER
*Commissioner of Patents and Trademarks*